(12) United States Patent
Park et al.

(10) Patent No.: US 11,090,501 B2
(45) Date of Patent: Aug. 17, 2021

(54) HEART PACEMAKER AND ENERGY HARVESTING METHOD THEREOF

(71) Applicant: KOREA ELECTRONICS TECHNOLOGY INSTITUTE, Seongnam-si (KR)

(72) Inventors: Hyun Moon Park, Gunpo-si (KR); Dong Sun Kim, Seongnam-si (KR); Tae Ho Hwang, Seoul (KR)

(73) Assignee: KOREA ELECTRONICS TECHNOLOGY INSTITUTE, Seongnam-si (KR)

( * ) Notice: Subject to any disclaimer, the term of this patent is extended or adjusted under 35 U.S.C. 154(b) by 300 days.

(21) Appl. No.: 16/209,400

(22) Filed: Dec. 4, 2018

(65) Prior Publication Data

US 2020/0147398 A1    May 14, 2020

(30) Foreign Application Priority Data

Nov. 12, 2018  (KR) .................... 10-2018-0138069
Nov. 12, 2018  (KR) .................... 10-2018-0138070

(51) Int. Cl.
*A61N 1/37*      (2006.01)
*A61N 1/378*     (2006.01)
*H02N 2/18*      (2006.01)
*A61N 1/375*     (2006.01)

(52) U.S. Cl.
CPC ......... *A61N 1/378* (2013.01); *A61N 1/37512* (2017.08); *H02N 2/186* (2013.01); *A61N 1/3756* (2013.01)

(58) Field of Classification Search
None
See application file for complete search history.

(56) References Cited

U.S. PATENT DOCUMENTS

| | | | |
|---|---|---|---|
| 2013/0161957 A1* | 6/2013 | Bhat | F03G 7/08 |
| | | | 290/53 |
| 2016/0331980 A1* | 11/2016 | Strommer | H02J 50/90 |
| 2017/0202738 A1* | 7/2017 | Greiner | A61N 1/37223 |
| 2018/0316280 A1* | 11/2018 | Niu | H02N 1/04 |
| 2019/0019632 A1* | 1/2019 | Rusling | H01G 11/36 |

FOREIGN PATENT DOCUMENTS

| | | |
|---|---|---|
| KR | 10-1053256 B | 8/2011 |
| KR | 10-2014-0136938 A | 12/2014 |
| KR | 10-1870278 B | 6/2018 |

OTHER PUBLICATIONS

Hyun-Moon Park et al., "A Development of P-EH(Practical Energy Harvester) Platform for Non-Linear Energy Harvesting Environment in Wearable Device", Journal of the KIECS, Oct. 31, 2018, pp. 1093-1100.

(Continued)

*Primary Examiner* — Ankit D Tejani
(74) *Attorney, Agent, or Firm* — Hauptman Ham, LLP

(57) ABSTRACT

A heart pacemaker according to the present invention includes a generator configured to generate nonlinear electrical energy using a friction element and an energy harvester configured to sequentially store the generated nonlinear electrical energy in multi-stage multiple energy storages and supply the electrical energy stored in the multiple energy storages.

14 Claims, 10 Drawing Sheets

(56) References Cited

OTHER PUBLICATIONS

Korean Office Action for corresponding Korean application No. 10-2018-0138070 dated Nov. 28, 2019, citing NPL No. 2.
Simiao Niu et al., A universal self-charging system driven by random biomechanical energy for sustainable operation of mobile electronics, Nature Communications, Published Dec. 11, 2015, DOI: 10.1038/ncomms9975, www.nature.com/naturecommunications.
Korean office action dated May 26, 2020, in connection with corresponding Korean Patent Application No. 10-2018-0138069.
Qiang Zheng et al. "In Vivo Powering of Pacemaker by Breathing-Driven Implanted Triboelectric Nanogenerator", Advanced Materials. 2014, 26, 5851-5856.

\* cited by examiner

HEART PACEMAKER AND ENERGY HARVESTING METHOD THEREOF

CROSS-REFERENCE TO RELATED APPLICATION

This application claims priority to and the benefit of Korean Patent Application No. 2018-0138069, filed on Nov. 12, 2018 and Korean Patent Application No. 2018-0138070, filed on Nov. 12, 2018, the disclosure of which is incorporated herein by reference in its entirety.

BACKGROUND

1. Field of the Invention

The present invention relates to a heart pacemaker and an energy harvesting method thereof.

2. Discussion of Related Art

A heart pacemaker is a device used to artificially maintain a normal heartbeat for various arrhythmia diseases, hemodynamic disorder, and conduction system disorder in which a heartbeat is not normal.

When a heart rhythm is abnormal, the heart pacemaker sends an electrical stimulus to the heart so that the heart can beat regularly and in time. The produced electrical stimulus is delivered to the heart through a special lead wire inserted into the heart.

The existing heart pacemaker is disadvantageous in that replacement with a new pacemaker is needed about every 10 years due to a limitation of a battery. At the end of the battery's lifespan, a patient should undergo surgery to replace an implanted heart pacemaker, which may cause a significant burden on the patient.

To overcome such drawbacks, existing heart pacemakers are being developed to reduce an amount of power used by using integrated semiconductors, but this approach cannot escape from fundamental energy consumption reduction of the heart pacemaker.

SUMMARY OF THE INVENTION

Embodiments of the present invention provide a heart pacemaker which allows a lifespan of a product to be increased by 50% or more by harvesting nonlinear electrical energy using a friction element inserted into the heart pacemaker, and an energy harvesting method of the heart pacemaker.

However, technical objectives to be achieved by the embodiments may not be limited to the above-described technical objectives, and there may be other technical objectives.

In a first aspect of the present invention, there is provided a heart pacemaker including a generator configured to generate nonlinear electrical energy using a friction element and an energy harvester configured to sequentially store the generated nonlinear electrical energy in multi-stage multiple energy storages and provide the electrical energy stored in the multiple energy storages.

The heart pacemaker may further include a case configured to protect the generator and the energy harvester The energy harvester may be disposed in parallel to a surface of an upper side of the case and the generator may be disposed on a lower side of the case and spaced a predetermined distance apart from a surface of the case.

The generator may be disposed to be spaced the predetermined distance apart from the surface of the case and a lowermost surface of the lower side of the case may be formed to have a curvature smaller than a curvature of the generator.

The generator may include a plurality of amplifying dampers formed on an outermost layer thereof.

The amplifying dampers, which increased the energy generation by a triboelectric nano-generator, it may be formed to have a size corresponding to the predetermined distance and attached to both surfaces of the case.

The amplifying dampers may maintain a fine movement of the friction element within a space formed by being spaced the predetermined distance apart from the case according to an external movement.

A plurality of elastic materials may be integrally formed within each of the amplifying dampers.

The friction element of the generator may be a triboelectric nano-generator.

The heart pacemaker may further include an electronic circuit configured to transmit an electrical signal via a lead wire and a battery configured to supply power to the electronic circuit.

The heart pacemaker may further include a communication module configured to transmit a heartbeat message to a diagnostic device through a wireless communication-based network.

The energy harvester may control the electrical energy to be sequentially stored in the multiple energy storages on the basis of a voltage of an energy storage in which the electrical energy is currently stored among the multiple energy storages and stability of the voltage.

The energy harvester may include a power manager configured to monitor a voltage generated in the friction element and voltages of the multiple energy storages and control a switching operation of a switch on the basis of the monitoring result such that the electrical energy is sequentially stored in the multiple energy storages.

When a deviation of a root mean square (RMS) voltage value of a currently charged energy storage among the multiple energy storages during a specific time period is greater than a predetermined value, the power manager may maintain the electrical energy so as to be stored in the currently charged energy storage.

The power manager may continuous discharge the multiple energy storages in response to an electrical energy supply request from a load.

In a second aspect of the present invention, there is provided an energy harvesting method of a heart pacemaker, the method including storing nonlinear electrical energy generated using a friction element in multiple energy storages, measuring voltage levels of the multiple energy storages, controlling the electrical energy to be continuous stored in the multiple energy storages on the basis of a voltage of an energy storage in which the electrical energy is currently stored and stability of the voltage, and supplying the electrical energy stored in the multiple energy storages.

In a third aspect of the present invention, there is provided a heart pacemaker for energy harvesting including a generator configured to generate nonlinear electrical energy using a friction element and an energy harvester comprising a temporary energy storage configured to temporarily store the generated electrical energy, multiple energy storages configured to receive and store the electrical energy temporarily stored in the temporary energy storage, and a power manager configured to sequentially store the electrical energy in the multiple energy storages on the basis of a voltage of an energy storage in which the electrical energy is currently stored among the multiple energy storages and stability of the voltage and supply the electrical energy stored in the multiple energy storages.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
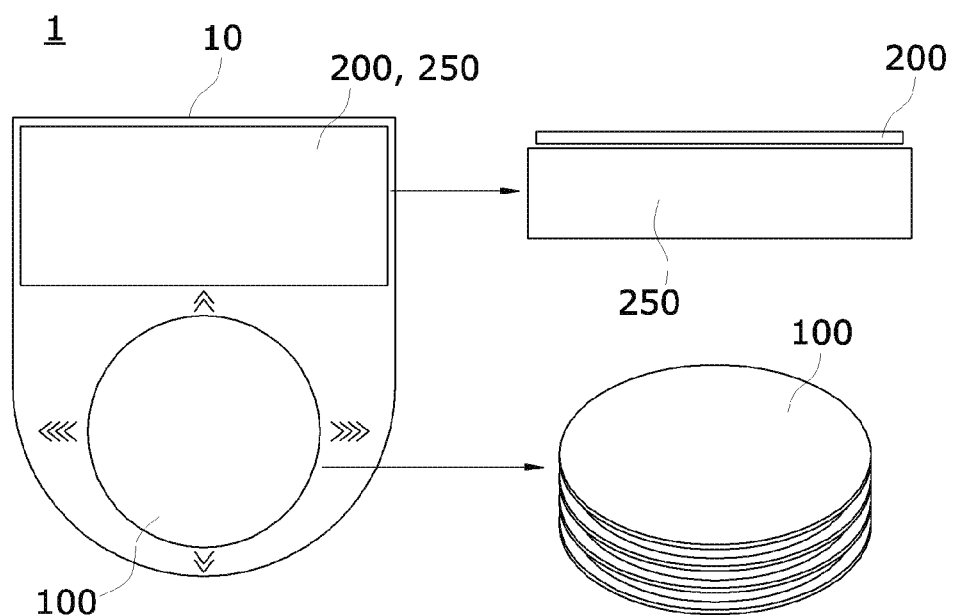
FIG. 1 is a diagram for describing a heart pacemaker according to one embodiment of the present invention.

The present invention will be described more fully hereinafter with reference to the accompanying drawings, in which exemplary embodiments of the invention are shown. The invention may, however, be embodied in many different forms and should not be construed as being limited to the embodiments set forth herein. Also, irrelevant details have been omitted from the drawings for increased clarity and conciseness, and similar parts are indicated by similar reference numerals throughout the detailed description.

Throughout the detailed description, unless explicitly described to the contrary, the word "comprise" and variations such as "comprises" or "comprising," will be understood to imply the inclusion of stated elements but not the exclusion of any other elements.

Figure 2:
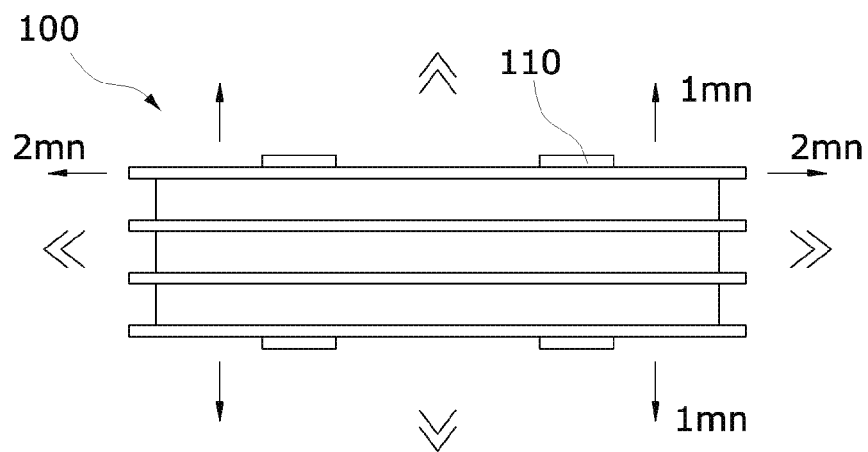
FIG. 2 is a diagram for describing a generator in one embodiment of the present invention.

FIG. 1 is a diagram for describing a heart pacemaker 1 according to one embodiment of the present invention. FIG. 2 is a diagram for describing a generator 100 in one embodiment of the present invention.

The heart pacemaker 1 capable of energy harvesting according to one embodiment of the present invention includes the generator 100 and an energy harvester 200.

In this case, the generator 100 and the energy harvester 200 may be embedded into a case 10 for the purpose of protection and the case 10 may be made of titanium. That is, the heart pacemaker 1 according to one embodiment of the present invention is characterized in that the generator 100 is inserted into the heart pacemaker 1 rather than being attached to a skin of a human body or inserted into a muscle tissue of the skin.

The generator 100 generates nonlinear electrical energy using a friction element. The friction element of the generator 100 may be a triboelectric nano-generator (TENG).

The energy harvester 200 sequentially stores the nonlinear electrical energy generated by the friction element of the generator 100 in multi-stage multiple energy storages 220 and supplies the energy stored in the multiple energy storages 220.

In this case, the multiple energy storages 220 are configured to be different from a battery 250 and are energy storages with small energy storage capacity which are configured integrally with an electronic circuit described below.

Referring to FIG. 1, the energy harvester 200 is disposed on an upper side of the case 10 of the heart pacemaker 1 and is disposed in parallel with one surface of the case 10. Here, the one surface of the case 10 at which the energy harvester 200 is positioned is the largest surface among a number of surfaces of the case 10. Accordingly, the energy harvester 200, the electronic circuit including the energy harvester 200, and the battery 250 are stacked atop each other and disposed in parallel with the largest surface of the case 10.

The generator 100 is disposed on a lower side of the case 10. That is, the energy harvester 200 is disposed on the upper side of the case 10 and the generator 100 is disposed on a lower part of the energy harvester 200 and spaced a predetermined distance apart from the surface of the case 10.

Specifically, the generator 100 is disposed to be spaced a predetermined distance apart from the surface of the case 10 of the heart pacemaker 1. In this case, the generator 100 may be formed to have a curvature greater than a curvature of the lowermost surface of a lower side of the case 10.

According to the above-described arrangement relations, the generator 100 may be inserted into the heart pacemaker 1 and generate nonlinear electrical energy.

Furthermore, in one embodiment of the present invention, the generator 100 may further include a plurality of amplifying dampers 110 formed on each of the outermost layers of the generator 100.

Each of the amplifying dampers 110 is formed to have a size corresponding to predetermined spacing between the surface of the case 10 of the heart pacemaker 1 and the generator 100 and attached to both surfaces of the case 10, and maintains a fine movement of the friction element within a space formed by being spaced a predetermined distance apart from the case 10 according to an external movement.

That is, a person performs activities through various movements, and the generator 100 to which the amplifying dampers 110 are attached generates electrical energy by such movements in daily life. While movements are being performed or even when the movement stops, the amplifying dampers 110 may maintain the fine movement of the friction element within the spaced space to maximize a characteristic of generation of electrical energy.

The amplifying dampers 110 attached to the generator 100 may maintain the fine movements in one or more directions of the up, down, left, and right directions corresponding to the various movements of the person.

Meanwhile, the amplifying dampers 110 may be formed of elastic Styrofoam having a predetermined elasticity or an elastic material, such as a rubber material, a spring material, or the like. In this case, in order to further maximize the fine movement, a plurality of elastic materials may be integrally formed within one amplifying damper 110.

For example, one amplifying damper 110 may be formed by one spring, or one amplifying damper 110 may be formed by a plurality of elastic materials having different radii in such a manner that a spring with a smaller radius is inserted into a spring having the largest radius.

In addition, as a fundamental configuration, the heart pacemaker 1 according to one embodiment of the present invention may further include the electronic circuit configured to transmit an electrical signal through a lead wire and the battery 250 configured to supply power to the electronic circuit. In this case, the circuit structure of the energy harvester 200 may be integrally formed with the electronic circuit and inserted into the heart pacemaker 1.

The electronic circuit may include a detector configured to detect heartbeat information of a human body, a tuner configured to adjust and supply a pulse signal transmitted through the lead wire, and a controller configured to control the detector and the tuner to enable accurate electrical stimulation.

In addition, the heart pacemaker 1 according to one embodiment of the present invention may further include a communication module configured to transmit a heartbeat message to an external diagnostic device through a wireless communication-based network.

In this case, the communication module applied to one embodiment of the present invention may further include a gain control apparatus 400 in a radio frequency (RF) transceiver using a phase shift keying (PSK) scheme and will be described below with reference to FIGS. 3A to 3C.

Figure 3A:
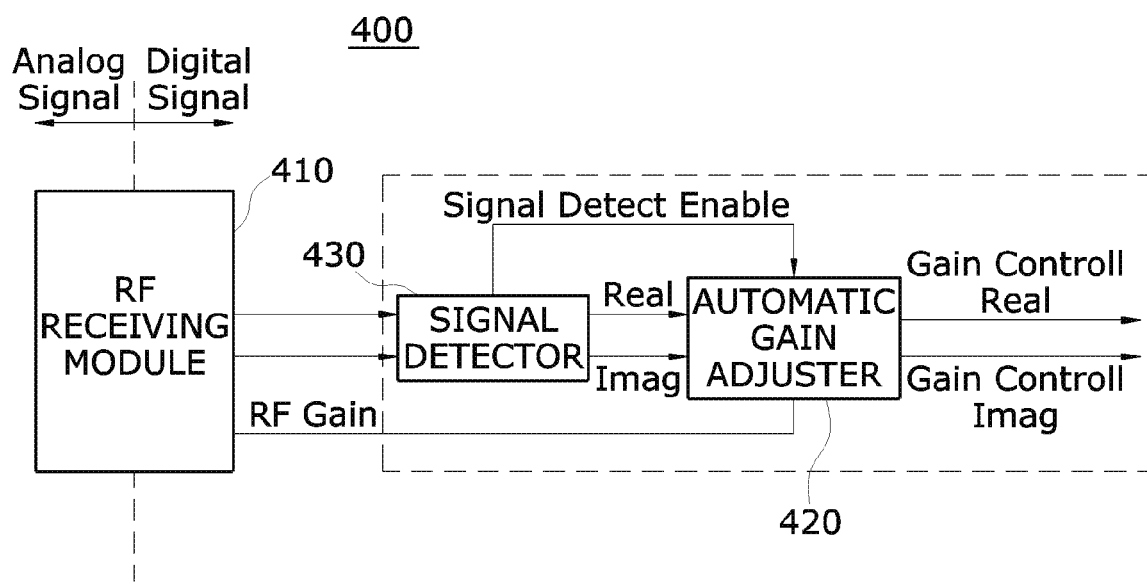
FIG. 3A is a block diagram illustrating a gain control apparatus applied in a communication module according to one embodiment of the present invention.
Figure 3B:
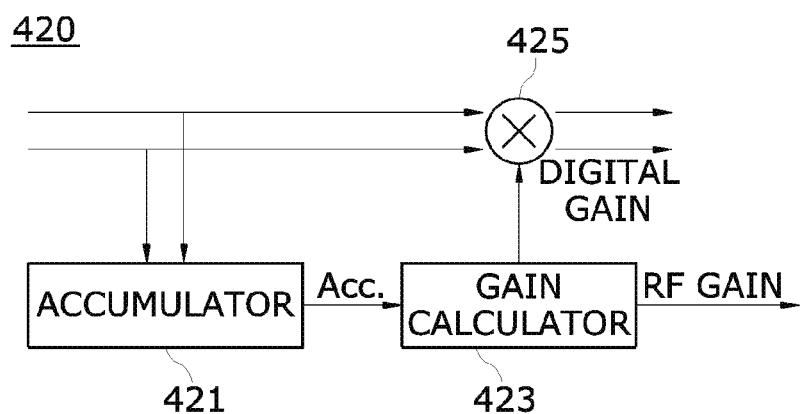
FIG. 3B is a block diagram illustrating an automatic gain adjuster.

FIG. 3A is a block diagram illustrating a gain control apparatus 400 applied in a communication module according to one embodiment of the present invention. FIG. 3B is a block diagram illustrating an automatic gain adjuster 420. FIG. 3C is a diagram for describing a process of adjusting a threshold value in a gain calculator 423.

The gain control apparatus 400 according to one embodiment of the present invention includes an RF receiving module 410 and the automatic gain adjuster 420.

The RF receiving module 410 receives an RF signal, which is an analog signal, and converts the RF signal into a digital signal in the form of a complex signal.

In this case, the RF receiving module 410 may receive the RF signal and convert the RF signal to a baseband frequency or an intermediate frequency, thereby converting it into a digital signal.

The automatic gain adjuster 420 calculates an RF gain for adjusting a gain of the RF signal and a digital gain for adjusting a gain of the digital signal and applies the calculated gains to the corresponding signals.

The automatic gain adjuster 420 may include an accumulator 421, the gain calculator 423, and a complex multiplier 425.

The accumulator 421 calculates a magnitude of the digital signal converted by the RF receiving module 410 and accumulates a predetermined number of digital signals. In this case, even when only one signal is received, the accumulator 421 may calculate the magnitude of a digital signal corresponding to the received signal and transmit the calculated magnitude to the gain calculator, but it may be preferable that the accumulator 421 accumulates a predetermined number of digital signals and thereafter calculates and transmits the magnitude of the digital signals.

That is, since many errors may temporarily occur in a gain to be obtained due to the impact of noise when the gain is determined for only one digital signal, the accumulator 421 accumulates a certain amount of data and adjusts a gain in consideration of the accumulated data.

As one embodiment, the accumulator 421 may accumulate 128 digital signals and provide the sum of magnitudes of the accumulated signals to the gain calculator 423.

The gain calculator 423 compares the magnitude of the accumulated digital signal with a predetermined threshold value and calculates an RF gain for adjusting a gain of the RF signal and a digital gain for adjusting a gain of a digital signal on the basis of the comparison result.

For example, a range of a gain obtainable by the gain calculator 423 may be from 22 to 100 dB, wherein a range of the RF gain may be from 22 to 81 dB and a gain of the digital gain may be from 0 to 19 dB.

In a case in which a current gain is 30 dB (RF gain=25 dB and digital gain=5 dB), when the gain is increased by 2 dB due to a small input signal, in one embodiment of the present invention, the RF gain may be adjusted to 27 dB and the digital gain may be maintained as it is, the RF gain may be adjusted to 26 dB and the digital gain may be adjusted to 6 dB, or the RF gain may be maintained as it is and the digital gain may be adjusted to 7 dB.

When the gain calculator 423 calculates the RF gain, the gain calculator 423 may feed the calculated RF gain back to the RF receiving module 410.

Accordingly, the RF receiving module 410 may apply the calculated RF gain to an RF signal, which is an analog signal, through an RF gain applier (not shown) included in the RF receiving module 410.

In this case, an available gain allowed by the RF receiving module 410 may be limited. That is, the RF gain applier may have a maximum applicable RF gain value set in advance. In addition, the RF gain applier applies the calculated RF gain to the RF signal within the maximum applicable RF gain value.

In this case, a desired signal may be obtained in a subsequent demodulation process only when a gain exceeding the RF gain value applicable by the RF gain applier is applied to the received RF signal. As a result, it may occur that a gain of the RF signal is insufficient.

To solve such a problem, in one embodiment of the present invention, the automatic gain adjuster 420 may calculate not only the RF gain but also a digital gain to be applied.

To this end, the automatic gain adjuster 420 may include the complex multiplier 425 configured to apply the digital gain to a digital signal.

In addition, when the RF gain fed back from the automatic gain adjuster 420 to the RF receiving module 410 satisfies the maximum applicable RF gain value, the RF signal to which the RF gain has been applied is converted into a digital signal and then the complex multiplier 425 applies a digital gain to the converted digital signal so that a gain value exceeding the RF gain value can be applied to the digital signal. By doing so, it may be anticipated that the stabilization performance of an RF receiver is faster than in a case where only the RF gain is controlled.

For example, when the maximum RF gain value applicable by the RF gain applier is 100 dB and the RF gain value fed back from the gain calculator 423 is 100 dB, a gain value necessary for extracting valid data of the received RF signal may be 110 dB.

In this case, the gain calculator 423 may control the RF gain to be adjusted to 100 dB and feed the adjusted RF gain back to the RF receiving module 410 and may control the digital gain to be adjusted to 10 dB and transmit the digital gain to the complex multiplier 425.

Accordingly, the RF gain applier of the RF receiving module 410 may convert the received RF signal into a digital signal after applying a gain of 100 dB to the RF signal, and the complex multiplier 425, which receives the converted digital signal, may apply a gain of 10 dB to the digital signal so that a total of 110-dB gain is applied to the digital signal and hence valid data extraction is possible.

As described above, one embodiment of the present invention is advantageous in that a digital gain can be additionally applied simultaneously when a gain exceeding a maximum gain range applicable to the RF receiving module 410 is required.

In addition, one embodiment of the present invention is advantageous in that, even when the maximum applicable RF gain value is not exceeded, a gain can be additionally applied to a digital signal in the feedback process without delay by applying a calculated digital gain to the digital signal in advance.

Meanwhile, in one embodiment of the present invention, a gain is controlled according to the magnitude of the accumulated signal. In this case, in order to compare a preset threshold value with the magnitude of the accumulated digital signal in the gain calculator 423 and to more quickly set a gain value to be adjusted, the preset threshold value may be classified into a plurality of classes, each of which is divided into steps, as shown in FIG. 3C.

Figure 3C:
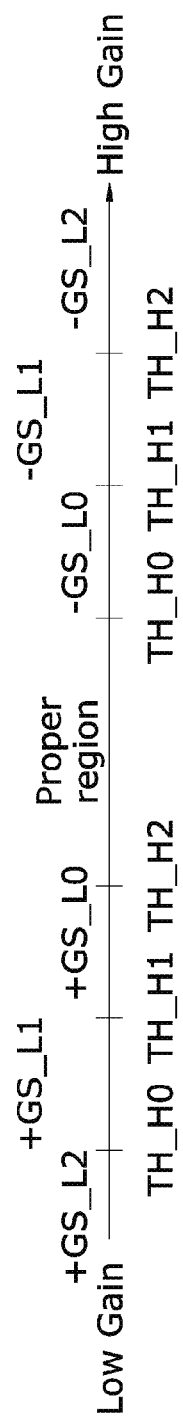
FIG. 3C is a diagram for describing a process of adjusting a threshold value in a gain calculator.

For example, FIG. 3C illustrates an example of a 3-step gain control, in which a gain is classified into a high gain, a low gain, and a proper gain, each of the high and low gains uses three threshold values, and gain adjustment values corresponding to the threshold values are allocated thereto.

Accordingly, the gain calculator 423 may select a class corresponding to the magnitude of the accumulated digital signal and the gain adjustment value corresponding to a step in the class, and adjust and calculate the previously applied RF gain and a gain of the digital signal through the selected gain adjustment value.

In addition, the gain control apparatus 400 according to one embodiment of the present invention may further include a signal detector 430.

The signal detector 430 may check whether the digital signal converted by the RF receiving module 410 is detected and drive the automatic gain adjuster 420 when it is confirmed that the digital signal is detected.

According to the configuration of the signal detector 430, in one embodiment of the present invention, the automatic gain adjuster 420 is driven by determining whether the signal is detected, thereby reducing power consumption.

As described above, the communication module included in the heart pacemaker may enable performance improvement of the receiver through the gain control apparatus including the hybrid automatic gain adjuster which simultaneously applies an analog gain and a digital gain to an RF signal, which is an analog signal, and a digital signal, respectively. In addition, when a gain to be adjusted is calculated, fast stabilization performance through comparison with a threshold value classified into a plurality of classes and steps may be expected.

Meanwhile, the heart pacemaker 1 according to one embodiment of the present invention naturally includes essential components for constituting the heart pacemaker 1 in addition to the aforementioned configuration, and it will be understood that various modifications can be made within a technical scope of the present invention.

Hereinafter, the energy harvester 200 configured to sequentially store nonlinear electrical energy through the multiple energy storages 220 and supply the electrical energy stored in the multiple energy storages 220 in the heart pacemaker 1 having the configurations of FIGS. 1 and 2 will be described in detail with reference to FIGS. 4 to 7.

Generally, an energy harvesting system stores, uses, and manages energy in a single energy storage. However, the following problems may occur due to a single integrated storage.

First, energy waste in the energy storage due to natural discharge may increase, energy may not be stored up to a required voltage level due to the nonlinear energy storage, and the stored energy may be easily discharged when there is no further energy generation from a harvester source. For these reasons, the rectification efficiency of the energy harvesting system is degraded.

Second, when output and charge occur simultaneously, in the case of a single energy storage, storage and output associated with conversion occur at the same time in one energy storage, and hence the complexity of control increases, which causes the efficiency to be reduced.

Third, when a voltage of the energy storage drops too much, the energy storage needs a large capacity for various operations in a load, and low voltage monitoring for the large capacity becomes less efficient as a quiescent current of the energy harvester increases, and accordingly, the energy harvester needs a storage time as a relatively high voltage is required to re-store the energy.

To solve such problems, the energy harvester 200 of the heart pacemaker 1 according to one embodiment of the present invention may store and manage the energy stepwise using the multiple energy storages 220, thereby improving the energy efficiency.

In addition, in harvesting irregular electrical energy occurring in the friction element, it is possible to increase the energy storage efficiency to a maximum level and actively manage the energy by supplying electrical energy in accordance with a request of a load.

Figure 4:
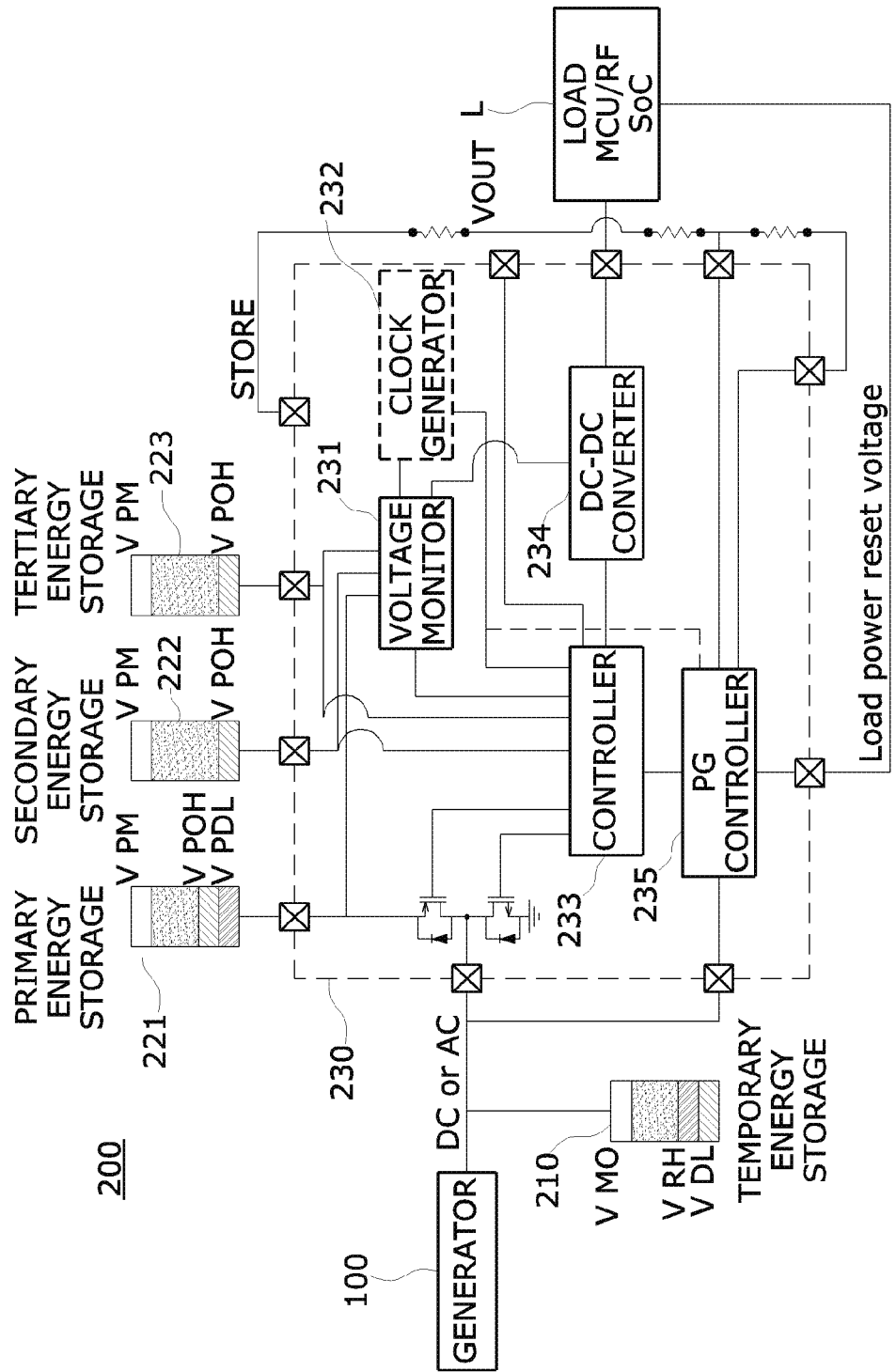
FIG. 4 is a diagram for describing an energy harvester in one embodiment of the present invention.

FIG. 4 is a diagram for describing the energy harvester 200 in one embodiment of the present invention.

The energy harvester 200 is configured to supply needed energy to a load L and includes the multiple energy storages 220 and a power manager 230.

The multiple energy storages 220 may include energy storages for receiving and storing electrical energy harvested by the generator 100.

In one embodiment of the present invention, the energy harvester 200 may control electrical energy to be sequentially stored in the multiple energy storages 220 on the basis of a voltage of an energy storage among the multiple energy storages 220 in which the electrical energy is currently stored and the stability of the voltage.

In FIG. 4, when storage of the electrical energy generated by the generator 100 is completed in a primary energy storage 221, the electrical energy is stored in a secondary energy storage 222. Once storage of the electrical energy is completed in the secondary energy storage 222, the electrical energy is stored in a tertiary energy storage 223.

As described above, in one embodiment of the present invention, the energy storage in the multiple energy storages 220 is performed stepwise.

Meanwhile, FIG. 4 illustrates that the multiple energy storages 220 include three energy storages, but this is merely one example. A plurality of energy storages may be provided as needed and capacities thereof may be varied.

The voltage levels of the multiple energy storages 220 may be classified into three types as shown below, and the three classified types may be set for each individual energy storage by a controller.

V_PDL (voltage preset detect low-voltage): lowest voltage at which the load L operates V_POH (voltage operation high-voltage): highest voltage at which the load L operates V_PM (voltage power good maximum-voltage): maximum voltage to be stored In addition, electrical energy supplied by one energy storage among the multiple energy storages 220 to the load L may be expressed as Equation 1 below.

$$E_c[J] = \tfrac{1}{2}cv^2 = \tfrac{1}{2} \times C_{Store} \times (VPOH^2 - VPDL^2) \qquad \text{[Equation 1]}$$

According to Equation 1, total electrical energy that can be supplied to the load L through the multiple energy storages 220 may be expressed as Equation 2 below.

$$E_c[J] = \tfrac{1}{2}cv^2 = \tfrac{1}{2}\{C_{Store^2} \times (VPOH_{Store^2}{}^2 - VPDL_{Store^2}{}^2) + C_{Store^2} \times (VPOH_{Store^2}{}^2 - VPDL_{Store^2}{}^2) + C_{Store^2} \times (VPOH_{Store^2}{}^2 - VPDL_{Store^2}{}^2)\} \qquad \text{[Equation 2]}$$

The power manager 230 monitors a voltage generated in the generator 100 and voltages of the multiple energy storages 220 and controls a switching operation on the basis of a monitoring result such that the electrical energy can be sequentially stored in the multiple energy storages 220.

In this case, when a deviation of a root mean square (RMS) voltage value of a currently charged energy storage among the multiple energy storages 220 during a specific time period is greater than a predetermined value, the power manager 230 may maintain the electrical energy to be stored in the currently charged energy storage.

In addition, the power manager 230 sequentially discharges the multiple energy storages 220 in response to an electrical energy supply request from the load L.

The power manager 230 includes a voltage monitor 231, a clock generator 232, a controller 233, a direct current (DC)-DC converter 234, and a power gate (PG) controller 235.

The voltage monitor 231 measures a voltage generated in the generator 100 and voltage levels of the multiple energy storages 220 and transmits the measurement result to the controller 233 and the DC-DC converter 234.

The clock generator 232 generates a clock and provides the clock to the voltage monitor 231, the controller 233, and the DC-DC converter 234 that need it.

The controller 233 controls switching between the multiple energy storages 220 for energy charging and switching between the multiple energy storages 220 and the DC-DC converter 234 for energy discharging. A detailed structure of the controller 233 is as shown in FIG. 4.

A switching control operation and process by control switch drivers of the controller 233 illustrated in FIG. 5 will be described below in detail with reference to FIG. 7.

The DC-DC converter 234 may convert a voltage of the electrical energy discharged from the multiple energy storages 220 through the controller 233 and apply the converted voltage to the load L. At this time, the DC-DC converter 234 refers to a voltage measurement result from the voltage monitor 231 for voltage conversion.

The PG controller 235 receives a power supply request from the load L and transmits the power supply request to the controller, and the controller 233 may establish a switching connection to the DC-DC converter 234 such that the multiple energy storages 220 sequentially discharge.

The discharging order of the multiple energy storages 220 is the same as the charging order. That is, discharging occurs in the order of the primary energy storage 221, the secondary energy storage 222, and the tertiary energy storage 223 according to a required amount of energy of the load L.

In addition, in a heart pacemaker 1 according to another embodiment of the present invention, an energy harvester 200 may further include a temporary energy storage 210.

A generator 100 generates nonlinear electrical energy using a friction element. A detailed configuration of the generator 100 has been described with reference to FIGS. 1 and 2, and thus a redundant description will be omitted.

The energy harvester 200 may include the temporary energy storage 210, multiple energy storages 220, and a power manager 230.

The temporary energy storage 210 temporarily stores the electrical energy harvested by the generator 100. In this case, a voltage level in the temporary energy storage 210 may be classified as follows.

V_DL (voltage detection low-voltage): a voltage at which quiescent current occurs V_RH (voltage requirement high-voltage): a voltage of a level at which the power manager can operate V_MO (voltage maximum point operation-voltage): a voltage that is the most efficient for the temporary energy storage 210 to discharge, which may be defined in advance by a manufacturer The multiple energy storages 220 include energy storages for receiving and storing electrical energy temporarily stored in the temporary energy storage 210, and the power manager 230 discharges the electrical energy stored in the temporary energy storage 210 so that the electrical energy is transmitted to the multiple energy storages 220. In addition, when there is a request from the load L, the power manager 230 sequentially discharges the energy stored in the temporary energy storage 210 and the multiple energy storages 220 and supplies the energy to the load L.

Meanwhile, when the power supply request is received from the load L, the above-described PG controller 235 forwards the power supply request to a controller 233 and discharges the electrical energy stored in the temporary energy storage 210 so as to apply the electrical energy to the load L.

For reference, the components illustrated in FIGS. 1 to 5 according to the embodiment of the present invention may be implemented in software or hardware, such as a field programmable gate array (FPGA) or an application specific integrated circuit (ASIC), and may perform predetermined functions.

However, the "components" are not limited to software or hardware, and each of the components may be configured to be stored in an addressable storage medium or to operate one or more processors.

Therefore, the components include, by way of examples, components, such as software components, object-oriented software components, and class components, processes, functions, attributes, procedures, subroutines, segments of a program code, drivers, firmware, microcode, circuitry, database, data structures, tables, arrays, and variables.

The components and the functionality provided in the components may be combined into fewer components or further separated into additional components.

Hereinafter, an energy harvesting method in the heart pacemaker 1 according to one embodiment of the present invention will be described with reference to FIGS. 6 and 7.

Figure 6:
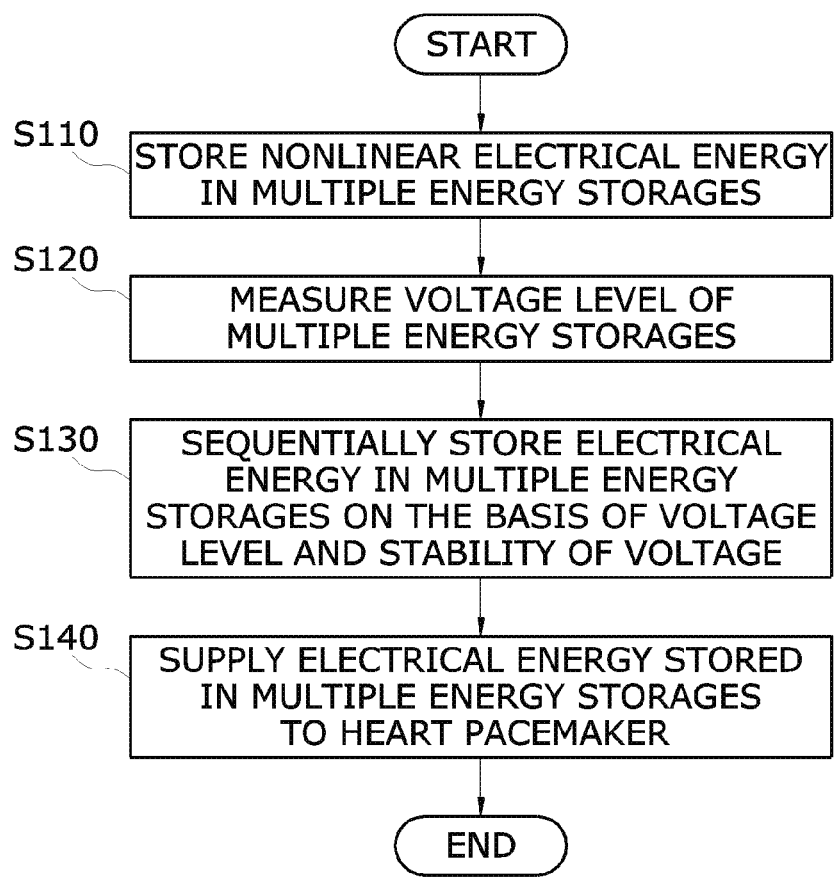
FIG. 6 is a flowchart illustrating an energy harvesting method in a heart pacemaker according to one embodiment of the present invention.

FIG. 6 is a flowchart illustrating an energy harvesting method in the heart pacemaker 1 according to one embodiment of the present invention.

In the energy harvesting method according to one embodiment of the present invention, nonlinear electrical energy generated using a friction element is stored in a plurality of energy storages (S110).

Then, voltage levels of the multiple energy storages 220 are measured (S120) and the electrical energy is controlled to be sequentially stored in the multiple energy storages 220 on the basis of a voltage of an energy storage in which electrical energy is currently stored and the stability of the voltages (S130).

Then, the electrical energy stored in the multiple energy storages 220 is supplied to the heart pacemaker 1 (S140).

Figure 5:
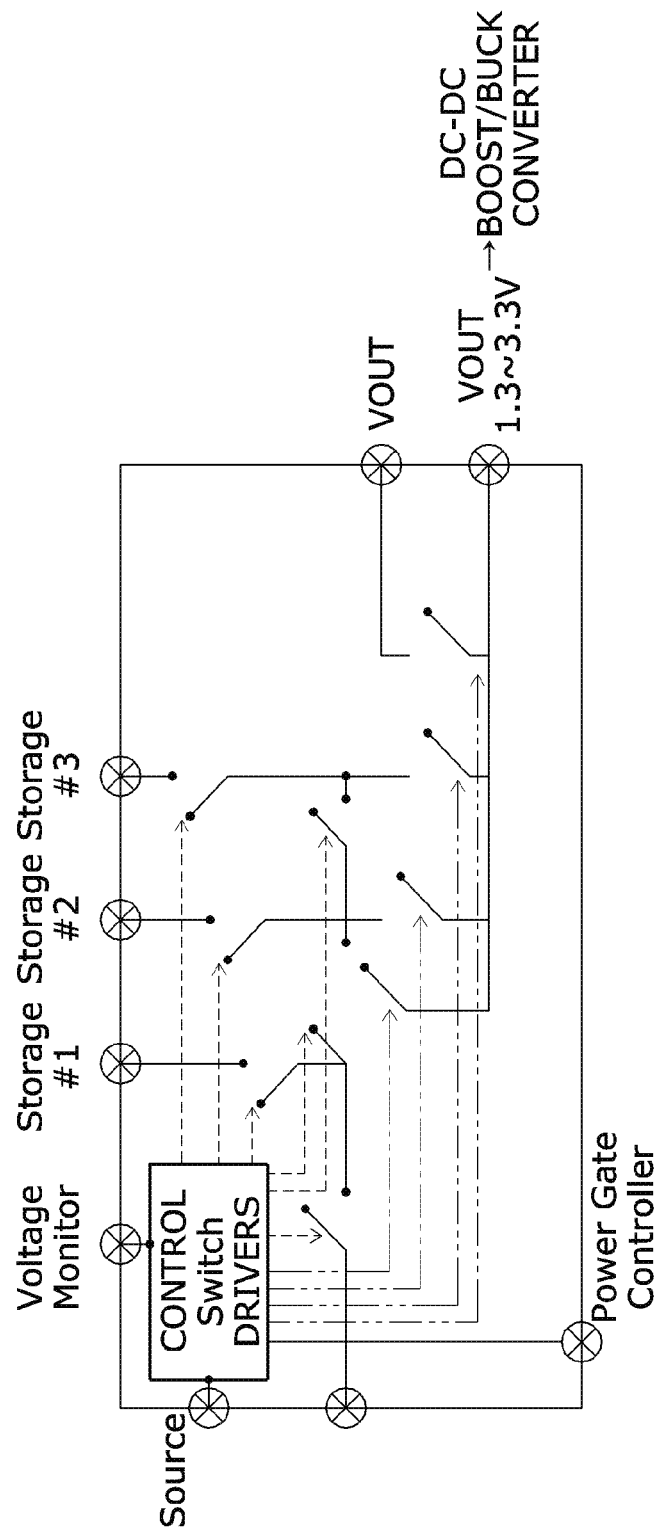
FIG. 5 is a diagram for describing a controller in one embodiment of the present invention.
Figure 7:
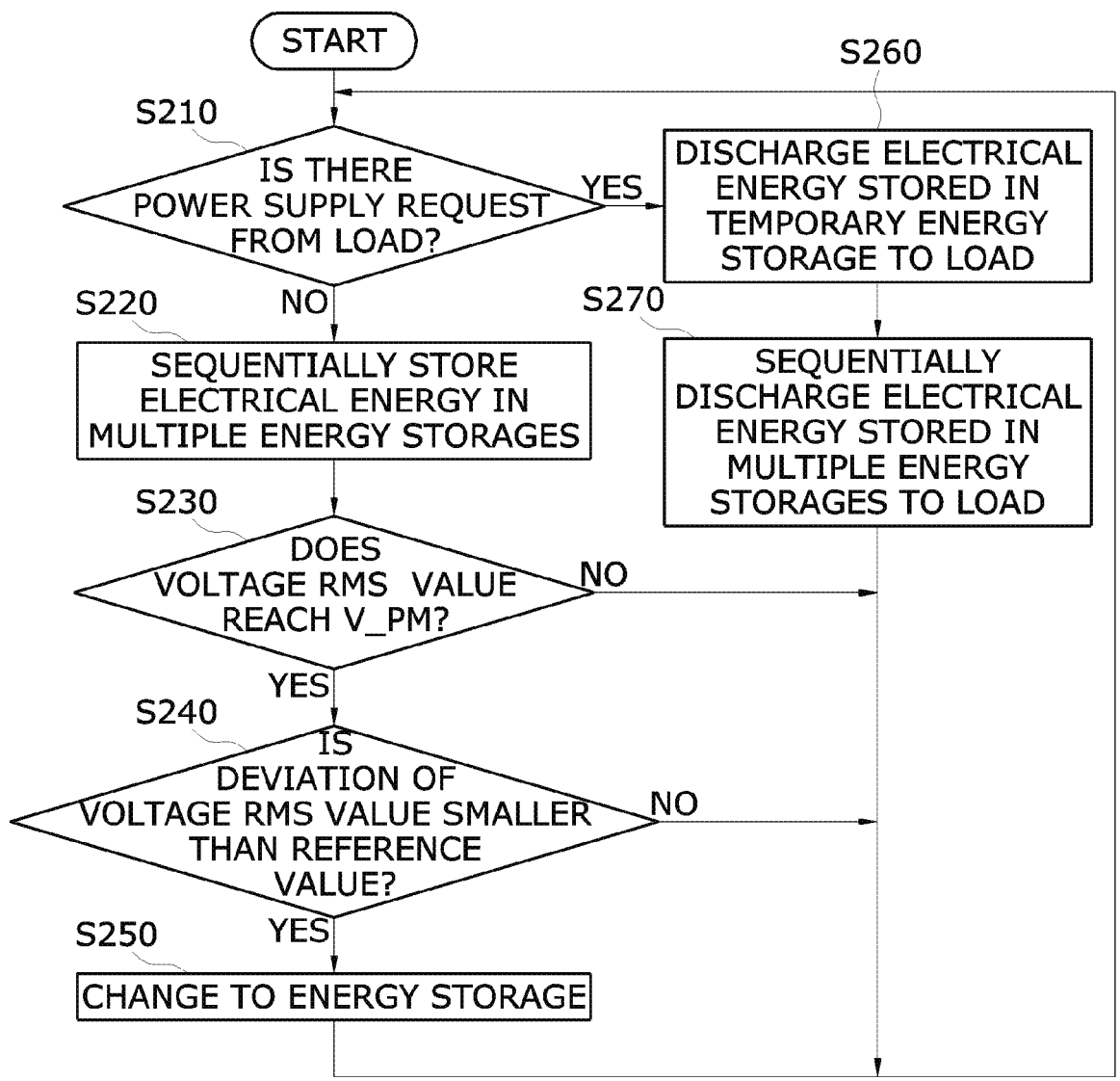
FIG. 7 is a flowchart for describing a switching control method performed by control switch drivers of the controller illustrated in FIG. 5.

FIG. 7 is a flowchart for describing a switching control method performed by control switch drivers of the controller 233 illustrated in FIG. 5.

When there is no power supply request from a load L (S210—NO), the multiple energy storages 220 are charged by connecting the multiple energy storages 220 and the temporary energy storage 210 (S220).

Specifically, the energy harvester 200 charges the multiple energy storages in the order of the primary energy storage 221, the secondary energy storage 222, and the tertiary energy storage 223, wherein the change of the energy storage is performed when charging of the previous energy storage is completed and the energy harvesting is stably performed in the temporary energy storage 210 (S230 to S250).

For example, in a state where a voltage RMS value of the primary energy storage 221 becomes V_PM, when a voltage of the temporary energy storage 210 is stable, a switching operation for connecting the temporary energy storage 210 to the secondary energy storage 222 is performed.

In a case where a voltage of the temporary energy storage 210 is not stable even when the voltage RMS value of the primary energy storage 221 reaches V_PM, it may be defined that the voltages of the temporary energy storage 210 and the primary energy storage 221 are stable when a deviation (variance or standard deviation) of a measured RMS voltage value of the primary energy storage 221 during a specified recent period is smaller than a predetermined reference value.

In a case where a voltage of the temporary energy storage 210 is not stable, that is, where a sufficient amount of energy is not harvested from the generator 100, if an energy storage to which the electrical energy of the temporary energy storage 210 is transferred is changed from the primary energy storage 221 to the secondary energy storage 222, it is not favorable in terms of overall energy efficiency since only natural discharge of the primary energy storage 221 occurs in a state where meaningful charging has not been performed in the secondary energy storage 222.

Meanwhile, when there is a power supply request from the load L (S210—YES), the PG controller 235 discharges the electrical energy stored in the temporary energy storage 210 and applies the electrical energy to the load (S260).

In addition, the controller 233 that has received the power supply request of the load L from the PG controller 235 sequentially establishes switching connections of the multiple energy storages 220 to the DC-DC converter 234 for electrical energy discharging (S270).

In the foregoing description, operations S110 to S270 may be further divided into more operations or combined into fewer operations according to embodiments of the present invention. In addition, some of the operations may be omitted if necessary, and the order of the operations may be changed. Further, any omitted descriptions of components or operations related to the heart pacemaker 1 described with reference to FIGS. 1 to 5 may be applied to the energy harvesting method described with reference to FIGS. 6 and 7.

Hereinafter, an energy harvester 300 according to another embodiment which is applied to the heart pacemaker 1 in accordance with one embodiment of the present invention will be described.

Figure 8:
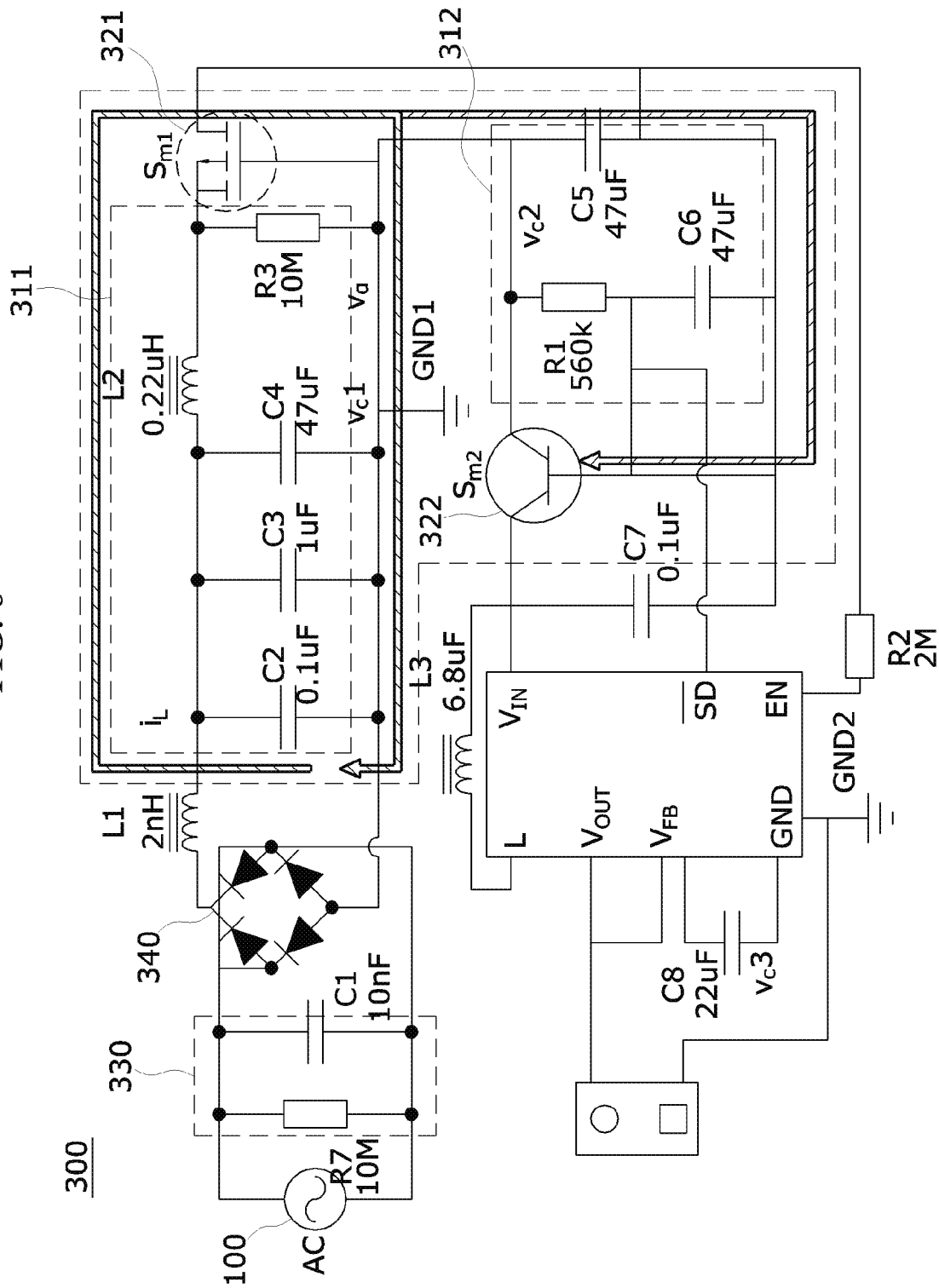
FIG. 8 is a diagram for describing an energy harvester applied to a heart pacemaker according to another embodiment of the present invention.

FIG. 8 is a diagram for describing an energy harvester 300 applied to the heart pacemaker 1 according to another embodiment of the present invention.

The energy harvester 300 that is applied to the heart pacemaker 1 according to another embodiment of the present invention includes a generator 100, multiple energy storages 310, and a switcher 320.

The generator 100 generates nonlinear electrical energy. The generator 100 may be a friction element, and the friction element may be a TENG.

The multiple energy storages 310 consist of multi-stage energy storages and store the nonlinear electrical energy generated by the generator 100.

Referring to FIG. 8, the multiple energy storages 310 may include a primary energy storage 311 and a secondary energy storage 312. In this case, FIG. 8 illustrates that the multiple energy storages 310 consist of two energy storages 311 and 312, but the embodiment is not limited thereto such that the multiple energy storages 310 may include a plurality of primary energy storages 311 and a plurality of secondary energy storages 312.

The primary energy storage 311 primarily stores electrical energy generated by the generator 100 through a low-pass filter consisting of a plurality of capacitors connected in parallel with each other and an inductor.

In the primary energy storage 311, the plurality of parallel-connected capacitors may have different capacities and be sequentially arranged in the increasing order of their capacity. For example, as shown in FIG. 8, the plurality of capacitors may have different capacities, such as 0.1 μF, 1 μF, and 47 μF, and be sequentially arranged in the increasing order of their capacity.

The parallel-connected capacitors in the primary energy storage 311 may be configured as three equivalent series inductor (ESL) and equivalent serial resistances (ESR) multilayer ceramic chip capacitors (MLCCs) for efficiency. In this case, inductance components and resistance components of the capacitors of the primary energy storage 311 may be provided by major manufacturers and a total impedance Zs may be calculated by Equations 3 and 4 below.

$$Zs = ESR + j\left[2\pi f \times ESL - \frac{1}{2\pi f}\right] \quad \text{[Equation 3]}$$

$$Zs = ESR + jXs \quad \text{[Equation 4]}$$

A composite impedance Xs may be expressed as Equation 5 below according to a definition of an approximate equation of the capacitor.

$$Xs \approx -\frac{1}{2\pi f \times c} \quad \text{[Equation 5]}$$

Based on the above equations, the resistance of the parallel-connected capacitors of the primary energy storage 311 may be obtained as about 0.01Ω within an impedance of 10 Hz. This is a very low resistance, which improves energy storage efficiency since a loss of stored energy is reduced to about ¹⁄₁₀ or more, as compared to the MLCC at the same frequency which has generally a resistance of 1 to 10Ω.

In addition, in the present invention, the electrical energy is received through a bridge diode circuit 340 located at a leading end of the primary energy storage 311, which converts alternate current (AC) electrical energy into DC electrical energy, and noise is removed from the converted electrical energy through a low-pass filter so that clean electrical energy can be stored.

Further, an energy harvester 300 according to still another embodiment of the present invention may further include an impedance matcher 330 configured to perform impedance matching between a plurality of capacitors and an inductor, which are included in the primary energy storage 311.

The secondary energy storage 312 consists of a plurality of parallel-connected capacitors and receives and stores the electrical energy stored in the primary energy storage 311.

In this case, the total capacity of the capacitors constituting the secondary energy storage 312 may be set to be greater than the total capacity of the capacitors constituting the primary energy storage 311.

Accordingly, as the electrical energy generated by the generator 100 is sequentially stored in the multiple energy storages 310, a voltage of electrical energy in each energy storage is sequentially lowered, and a current of the electrical energy is sequentially increased with the sequential decrease of the voltage so that the multiple energy storages 310 of the present invention may serve as a current booster.

The switcher 320 includes a first switch 321 and a second switch 322, stores the electrical energy sequentially in the multiple energy storages through a switching operation, and supplies the stored energy to the load. In this case, the numbers of first switches 321 and second switches 322 of the switcher 320 may correspond to the number of energy storages constituting the multiple energy storages 310.

The first switch 321, which is a metal-oxide-semiconductor field-effect transistor (MOSFET)-based switch, performs switching such that the electrical energy stored in the primary energy storage 311 is discharged and transferred to the secondary energy storage 312.

When a current voltage of the primary energy storage 311 is smaller than or equal to a previous voltage, the first switch 321 is switched off such that the primary energy storage 311 is charged. When the current voltage of the primary energy storage 311 is greater than the previous voltage, a current voltage of the first switch 321 is compared with a threshold voltage, and when the current voltage is greater than the threshold voltage, the first switch 321 is switched on such that the primary energy storage 311 discharges the currently stored energy.

In this case, the first switch 321 is driven in an ON state for a predetermined period of time when a preset first voltage range of the primary energy storage 311 is detected.

The second switch 322 may perform switching such that the electrical energy stored in the secondary energy storage 312 is transferred to the load. In this case, the second switch 322, which is a multi-switch, may have an integrated circuit (IC) region including a voltage comparator.

Similarly to the first switch 321, when a current voltage of the secondary energy storage 312 is smaller than or equal to a previous voltage, the second switch 322 is switched off such that the secondary energy storage 312 is charged. When the current voltage of the secondary energy storage 312 is greater than the previous voltage, a current voltage of the second switch 322 is compared with a threshold voltage, and when the current voltage is greater than the threshold voltage, the second switch 322 is switched on such that the secondary energy storage discharges the currently stored energy to the load.

At this time, when a preset second voltage range of the secondary energy storage 312 is detected, the second switch 322 is driven in the ON state for a predetermined period of time. In this case, the first voltage range of the primary energy storage 311 is set to be greater than the second voltage range of the secondary energy storage 312.

The first and second switches 321 and 322 may be configured as n-channel MOSFET (NMOS)-based switches.

In addition, the switcher 320 may check an amount of vibration of the generator 100 through monitoring of electrical energy generated over time in the multiple energy storages 310.

Meanwhile, generated energy (in $J_{oc}$, open circuit Joule) generated by the generator 100 that generates nonlinear electrical energy is high in voltage and low in power, and in the case of non-periodic generated energy, the voltage that is decreased in the form of a certain sine wave is generated.

Accordingly, as described above, the primary energy storage $st^1$ 311 is composed of a plurality of capacitors having a very low resistance for continuous energy storage while lowering the voltage.

In addition, primarily stored energy $J_{st1}$ allows Max power to be transformed to the secondary energy storage $st^2$ 312 while the first switch 321 is repeatedly switched ON/OFF through monitoring of the voltage generated in the generator 100. The Max power is ultimately defined as energy stored in the primary energy storage 311.

The energy harvester 300 according to still another embodiment of the present invention suggests buck and booster conversion which is required for power conversion, depending on an existing generated energy condition, and also suggests a single conversion circuit serving as a current booster consisting of the multiple energy storages 310, thereby enabling simplification and increasing a conversion rate.

Meanwhile, according to yet another embodiment of the present invention, the energy harvester 300 may operate as a current booster.

The current booster includes a generator, a plurality of primary capacitors, an inductor, a first switch, a plurality of secondary capacitors, and a second switch.

The generator generates nonlinear electrical energy.

The plurality of primary capacitors having different parallel capacities are arranged in parallel to each other such that the capacity is sequentially increased, and the primary capacitors receive the electrical energy from the generator and primarily amplify a current.

The inductor is serially connected to the plurality of primary capacitors and operates as a low-passband filter.

The first switch discharges the electrical energy stored in the primary capacitors to the secondary capacitors through a switching operation when a current voltage of the primary capacitors is greater than or equal to a first switching voltage.

The plurality of secondary capacitors receive the electrical energy stored in the primary capacitors and secondarily amplify the current. At this time, the total capacity of the secondary capacitors is greater than the total capacity of the primary capacitors.

The second switch discharges the electrical energy stored in the secondary capacitors to a load through a switching operation when a voltage of the secondary capacitors is greater than or equal to a second switching voltage that is smaller than the first switching voltage.

In the current booster according to one embodiment of the present invention, the voltage is sequentially lowered from the primary capacitors to the secondary capacitors while the current is amplified and sequentially increased.

Meanwhile, a current booster according to still another embodiment of the present invention shares the technical characteristics with the energy harvester 300 according to another embodiment of the present invention, and hence a detailed description thereof will be replaced with the description of the energy harvester 300.

Hereinafter, a switching operation performed in the above-described current booster and the energy harvester 300 serving as the current booster will be described with reference to FIG. 9A and FIG. 9B.

Figure 9A:
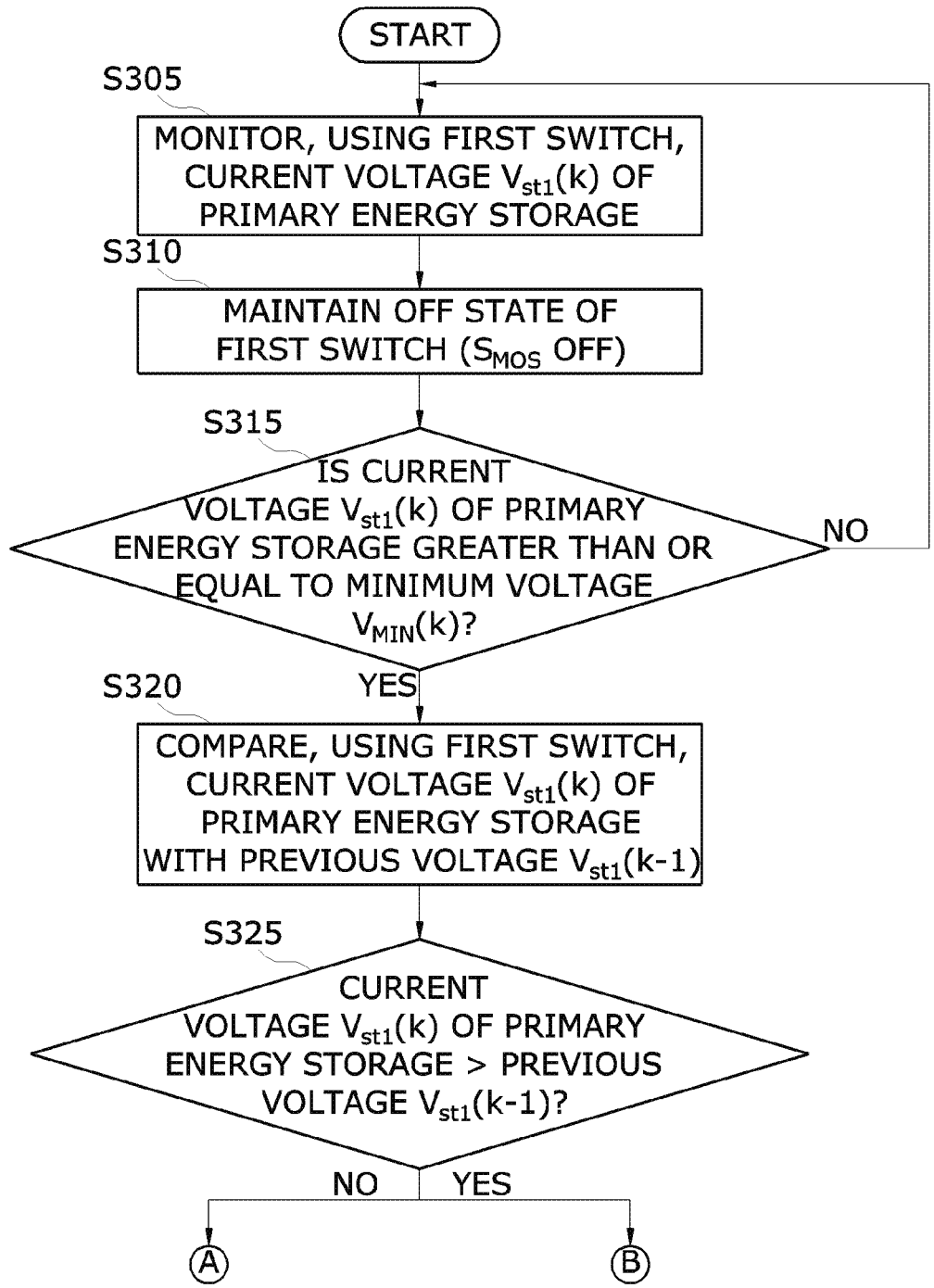
FIG. 9A and FIG. 9B are diagram for describing a switching operation in a current booster and an energy harvester.
Figure 9B:
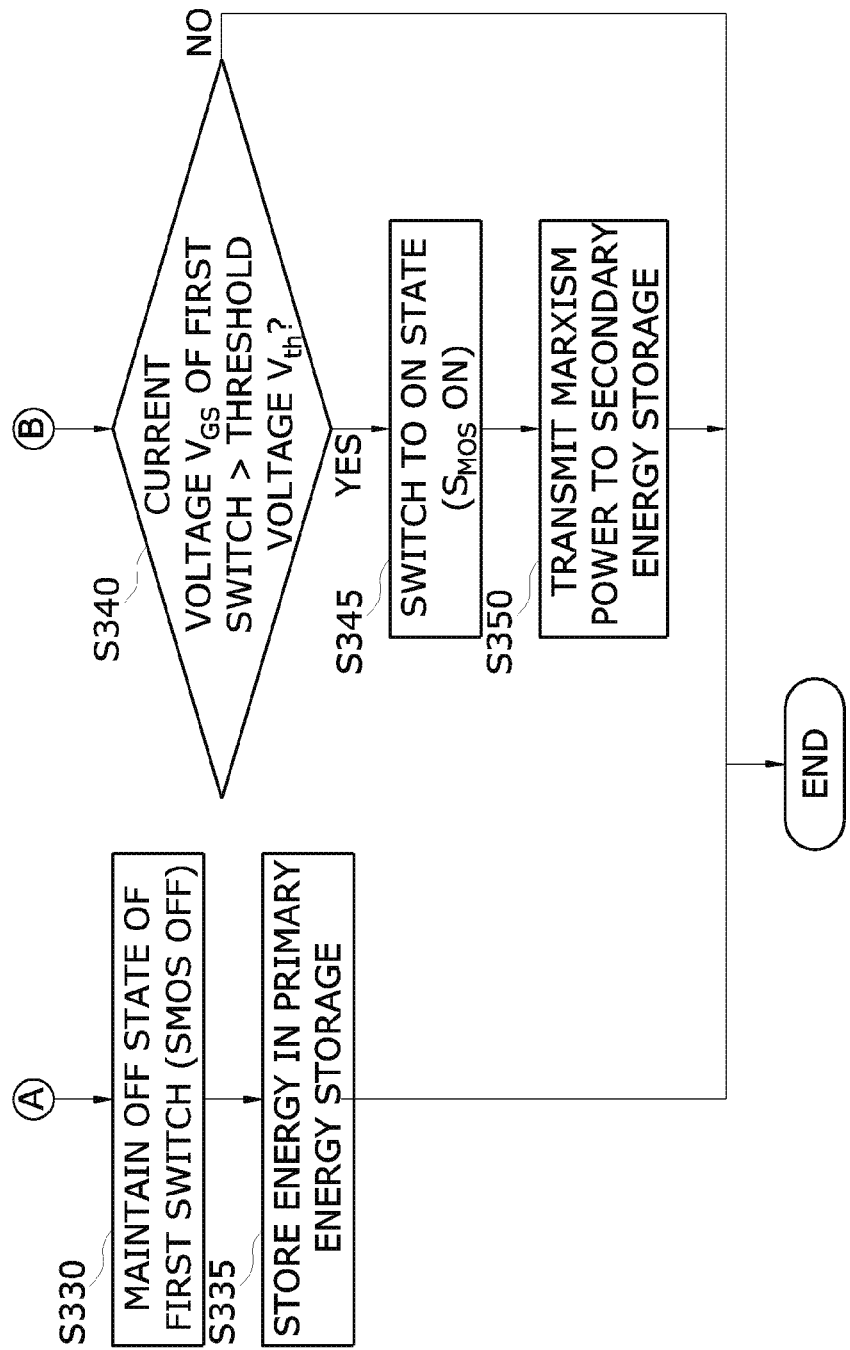

FIG. 9A and FIG. 9B are diagram for describing a switching operation in the current booster and the energy harvester 300.

First, the first switch 321 monitors a current voltage $V_{st1}(k)$ of the primary energy storage 311 (S305). At this time, the first switch 321 remains in an open state (S310).

The monitoring process is continuously performed when the current voltage $V_{st1}(k)$ is less than a minimum voltage VMIN(k) (S315—NO).

On the contrary, when the current voltage $V_{st1}(k)$ is greater than or equal to the minimum voltage VMIN(k) (S315—YES), the first switch 321 compares the current voltage $V_{st1}(k)$ of the primary energy storage 311 with a previous voltage $V_{st1}(k-1)$ (S320).

When the comparison result indicates that the current voltage $V_{st1}(k)$ of the primary energy storage 311 is smaller than the previous voltage $V_{st1}(k-1)$ (S325—NO), the first switch 321 remains in an open state (S330) so that the voltage is continuously stored in the primary energy storage 311 (S335).

On the contrary, when the comparison result indicates that the current voltage $V_{st1}(k)$ of the primary energy storage 311 is greater than the previous voltage $V_{st1}(k-1)$ as shown in Equation 6 (S325—YES), it is determined on the basis of Equation 7 whether a current voltage $V_{GS}$ of the first switch $S_{MOS}$ 321 is greater than a threshold voltage $V_{th}$ (S340).

$$V_{st1}(k)-V_{st1}(k-1)>0 \qquad \text{[Equation 6]}$$

$$V_{GS}>V_{th}, V_{DS}<V_{GS}-V_{th} \qquad \text{[Equation 7]}$$

When it is determined that the current voltage $V_{GS}$ of the first switch $S_{MOS}$ 321 is greater than the threshold voltage $V_{th}$ (S340—YES), the first switch 321 is switched to the ON state (S345) and transmits tracking power to the secondary energy storage 312 (S350).

At this time, the first switch 321 is driven in the ON state for a predetermined period of time when a preset first voltage $V_{st1\_ref}$ of the primary energy storage 311 is detected. The preset first voltage $V_{st1\_ref}$ of the primary energy storage 311 refers to a limit voltage in a switch short-circuit state at the current voltage $V_{st1}(k)$.

A voltage $\Delta V_{st1}(k)$ collected for a predetermined period of time in the ON state of the first switch 321 may be expressed as Equation 8 that represents a voltage that is stored until the first switch 321 is switched to OFF state.

$$V_{st2}(J)=\Delta V_{st1}(k)-V_{ref\text{-}st1} \qquad \text{[Equation 8]}$$

Meanwhile, the preset first voltage $V_{st1\_ref}$ of the primary energy storage 311 must be higher than a preset second voltage $V_{st2\_ref}$ of the secondary energy storage 312, and the total sum $\Delta V_{st2}(\Sigma_o^n J_i)$ of voltage $(\Delta V_{st2}(J))$ collected from the primary energy storage 311 for a predetermined period of time must be lower than the preset second voltage $V_{st2\_ref}$ of the secondary energy storage 312.

When a voltage of, for example, 1.33 to 1.37 V is input to the secondary energy storage $st^2$ 312, ON/OFF states of the second switch 322 are repeated the same as those of the first switch 321 connected to the primary energy storage 311 and the second switch 322 transfers energy to a DC-DC booster.

According to the above-described method, one embodiment of the present invention uniformly stores a voltage and a current in accordance with a change of generated electrical energy as energy and lowers the voltage, thereby internally simplifying a complex IC structure including a charge buck, a multi-stage MOS switch, an inductor, and the like for existing high-voltage operations so that complexity of a power management IC (PMIC) can be lowered.

In addition, a space of the energy storage is freely adjusted by using the multiple energy storages 310 and the PMIC or DC-DC converter is used through a current booster, which is a single mode, thereby increasing efficiency.

Consequently, according to one embodiment of the present invention, it is possible to reduce energy loss from the generator 100, which is a source of generation, and provide high efficiency in using a PMIC.

Meanwhile, an operation method of the second switch 322 is performed in the same manner as in the first switch 321, and thus a detailed description thereof will be omitted.

In the above description, operations S310 to S350 may be further divided into more operations or combined into fewer operations according to embodiments of the present invention. In addition, some of the operations may be omitted if necessary, and the order of the operations may be changed. Further, any omitted descriptions of components or operations related to the energy harvester 300 described with reference to FIG. 8 may be applied to the method described with reference to FIG. 9A and FIG. 9B.

According to one embodiment of the present invention, the multiple energy storages allow stepwise storage and management of energy generated in a source so that it is possible to improve energy efficiency even in a condition where energy supply is irregular.

In addition, in a situation where energy harvesting is irregular and unstable, it is possible to provide a more active supply of power to a source, thereby offering an energy distribution scheme for supersaturated and irregular energy generation situations. Also, an energy supply situation of an external environment is inferred through continuous monitoring of a correlation between voltages of a plurality of energy storages and time, and the inference result is provided through various switching schemes so that a more aggressive supply of energy from the energy harvester is possible.

Furthermore, it is possible to more actively control a starting voltage on a platform and to perform alternate charging within a starting voltage range in accordance with a complex storage so that a system consisting of a booster and a buck can be replaced with a single system controlled by various switches in an operation period according to a current voltage level.

One embodiment of the present invention may be implemented in the form of a computer program stored in a medium executed by a computer or a recording medium that includes computer executable instructions. A computer-readable medium may be any usable medium that can be accessed by a computer and may include all volatile and nonvolatile media and detachable and non-detachable media. Also, the computer-readable medium may include all computer storage media and communication media. The computer storage medium includes all volatile and nonvolatile media and detachable and non-detachable media implemented by a certain method or technology for storing information such as computer-readable instructions, data structures, program modules, or other data. The communication medium typically includes computer-readable instructions, data structures, program modules, other data of a modulated data signal such as a carrier wave or other transmission mechanisms, and includes information transmission media.

The method and system of the present invention have been described in connection with specific embodiments of the invention, and some or all of the components or operations thereof may be realized using a computer system that has hardware architecture for general-use.

The foregoing description of the invention is for illustrative purposes, and a person having ordinary skilled in the art will appreciate that other specific modifications can be easily made without departing from the technical spirit or essential features of the invention. Therefore, the foregoing embodiments should be regarded as illustrative rather than limiting in all aspects. For example, each component described as being of a single type can be implemented in a distributed manner. Likewise, components described as being distributed can be implemented in a combined manner.

The scope of the present invention is not defined by the detailed description as set forth above but by the accompanying claims of the invention. It should also be understood that all changes or modifications derived from the definitions and scopes of the claims and their equivalents fall within the scope of the invention.

What is claimed is:

1. A heart pacemaker comprising:
a generator configured to generate nonlinear electrical energy using a friction element;
an energy harvester configured to sequentially store the generated nonlinear electrical energy in multi-stage multiple energy storages and provide the electrical energy stored in the multiple energy storages; and
a case configured to protect the generator and the energy harvester,
wherein the generator includes a plurality of amplifying dampers formed on an outermost layer thereof; and
wherein the plurality of amplifying dampers maintain a fine movement of the friction element within a space formed by being spaced a predetermined distance apart from the case according to an external movement.

2. The heart pacemaker of claim 1, wherein the energy harvester is disposed in parallel to a surface of an upper side of the case and the generator is disposed on a lower side of the case and spaced the predetermined distance apart from a surface of the case.

3. The heart pacemaker of claim 2, wherein the generator is disposed to be spaced the predetermined distance apart from the surface of the case and a lowermost surface of the lower side of the case is formed to have a curvature smaller than a curvature of the generator.

4. The heart pacemaker of claim 1, wherein the amplifying dampers are formed to have a size corresponding to the predetermined distance and attached to both surfaces of the case.

5. The heart pacemaker of claim 1, wherein a plurality of elastic materials are integrally formed within each of the amplifying dampers.

6. The heart pacemaker of claim 1, wherein the friction element of the generator is a triboelectric nano-generator.

7. The heart pacemaker of claim 1, further comprising:
an electronic circuit configured to transmit an electrical signal via a lead wire; and
a battery configured to supply power to the electronic circuit.

8. The heart pacemaker of claim 1, further comprising a communication module configured to transmit a heartbeat message to a diagnostic device through a wireless communication-based network.

9. The heart pacemaker of claim 1, wherein the energy harvester controls the electrical energy to be sequentially stored in the multiple energy storages on the basis of a voltage of an energy storage in which the electrical energy is currently stored among the multiple energy storages and stability of the voltage.

10. The heart pacemaker of claim 9, wherein the energy harvester includes a power manager configured to monitor a voltage generated in the friction element and voltages of the multiple energy storages and control a switching operation of a switch on the basis of the monitoring result such that the electrical energy is sequentially stored in the multiple energy storages.

11. The heart pacemaker of claim 10, wherein when a deviation of a root mean square (RMS) voltage value of a currently charged energy storage among the multiple energy storages during a specific time period is greater than a predetermined value, the power manager maintains the electrical energy so as to be stored in the currently charged energy storage.

12. The heart pacemaker of claim 10, wherein the power manager continuous discharges the multiple energy storages in response to an electrical energy supply request from a load.

13. An energy harvesting method of the heart pacemaker configured according to claim 1, the method comprising:
storing nonlinear electrical energy generated using a friction element in multiple energy storages;
measuring voltage levels of the multiple energy storages;
controlling the electrical energy to be continuous stored in the multiple energy storages on the basis of a voltage of an energy storage in which the electrical energy is currently stored and stability of the voltage; and
supplying the electrical energy stored in the multiple energy storages.

14. A heart pacemaker for energy harvesting, comprising:
a generator configured to generate nonlinear electrical energy using a friction element;
an energy harvester comprising a temporary energy storage configured to temporarily store the generated electrical energy, multiple energy storages configured to receive and store the electrical energy temporarily stored in the temporary energy storage, and a power manager configured to sequentially store the electrical energy in the multiple energy storages on the basis of a voltage of an energy storage in which the electrical energy is currently stored among the multiple energy storages and stability of the voltage and supply the electrical energy stored in the multiple energy storages; and
a case configured to protect the generator and the energy harvester,
wherein the generator includes a plurality of amplifying dampers formed on an outermost layer thereof; and
wherein the plurality of amplifying dampers maintain a fine movement of the friction element within a space formed by being spaced a predetermined distance apart from the case according to an external movement.

* * * * *